(12) United States Patent
Santra et al.

(10) Patent No.: US 11,001,585 B2
(45) Date of Patent: May 11, 2021

(54) CRYSTALLINE FORMS OF IBRUTINIB

(71) Applicant: SUN PHARMACEUTICAL INDUSTRIES LIMITED, Maharashtra (IN)

(72) Inventors: Ramkinkar Santra, Paschim Medinipur (IN); Bala Krishna Reddy Bhogala, Kadapa (IN); Chandra Has Khanduri, Gurgaon (IN)

(73) Assignee: SUN PHARMACEUTICAL INDUSTRIES LIMITED, Maharashtra (IN)

( * ) Notice: Subject to any disclaimer, the term of this patent is extended or adjusted under 35 U.S.C. 154(b) by 0 days.

(21) Appl. No.: 15/753,680

(22) PCT Filed: Aug. 10, 2016

(86) PCT No.: PCT/IB2016/054823
§ 371 (c)(1),
(2) Date: Feb. 20, 2018

(87) PCT Pub. No.: WO2017/029586
PCT Pub. Date: Feb. 23, 2017

(65) Prior Publication Data
US 2019/0002468 A1 Jan. 3, 2019

(30) Foreign Application Priority Data
Aug. 19, 2015 (IN) .............. 2558/DEL/2015

(51) Int. Cl.
*C07D 487/04* (2006.01)
*A61P 35/00* (2006.01)
(52) U.S. Cl.
CPC ............ *C07D 487/04* (2013.01); *A61P 35/00* (2018.01); *C07B 2200/13* (2013.01)
(58) Field of Classification Search
CPC .................................................. C07D 487/04
See application file for complete search history.

(56) References Cited

U.S. PATENT DOCUMENTS

| 7,514,444 B2 | 4/2009 | Honigberg et al. | |
|---|---|---|---|
| 2008/0108636 A1 | 5/2008 | Honigberg et al. | |
| 2015/0140085 A1* | 5/2015 | Goldstein | A61K 45/06 424/452 |
| 2017/0002009 A1* | 1/2017 | Chen | C07D 487/04 |
| 2017/0226108 A1* | 8/2017 | Adin | A61K 31/519 |

FOREIGN PATENT DOCUMENTS

| CN | 103923084 A | 7/2014 |
|---|---|---|
| CN | 104327085 | 2/2015 |
| CN | 104447761 | 3/2015 |
| KR | 10-2018-700767 A | 5/2018 |
| KR | 1020180040694 A | 5/2018 |
| WO | 2013/184572 A1 | 12/2013 |
| WO | 2015/081180 A1 | 6/2015 |
| WO | 2015/145415 A2 | 10/2015 |
| WO | 2016/139588 A1 | 9/2016 |
| WO | 2016/160598 A | 10/2016 |

OTHER PUBLICATIONS

International Search Report and Written Opinion dated Dec. 8, 2016 for PCT Application No. PCT/IB2016/054823.
International Preliminary Report on Patentability dated Mar. 1, 2018 for PCT Application No. PCT/IB2016/054823.
Extended Search report dated Dec. 12, 2018 for application No. 16836715.9.

* cited by examiner

*Primary Examiner* — Matthew P Coughlin
(74) *Attorney, Agent, or Firm* — Blank Rome LLP

(57) ABSTRACT

The present invention relates to crystalline forms of ibrutinib, designated as Form S1, Form S2, Form S3, Form S4, and an amorphous form, designated as Form A1, and processes for their preparation, pharmaceutical compositions comprising these forms, and their use for the treatment of Bruton's tyrosine kinase (BTK) mediated diseases.

15 Claims, 16 Drawing Sheets

CRYSTALLINE FORMS OF IBRUTINIB

FIELD OF THE INVENTION

The present invention relates to crystalline forms of ibrutinib, designated as Form S1, Form S2, Form S3, Form S4, and an amorphous form, designated as Form A1, and processes for their preparation, pharmaceutical compositions comprising these forms, and their use for the treatment of Bruton's tyrosine kinase (BTK) mediated diseases.

BACKGROUND OF THE INVENTION

Ibrutinib chemically is 1-[(3R)-3-[4-amino-3-(4-phenoxyphenyl)-1H-pyrazolo[3,4-d]pyrimidin-1-yl]-1-piperidinyl]-2-propen-1-one, represented by Formula I.

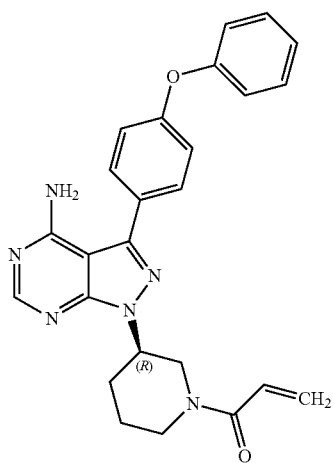

Formula I

Ibrutinib is an inhibitor of Bruton's tyrosine kinase (BTK).

PCT Publication No. WO 2008/039218 discloses ibrutinib and a process for its preparation.

PCT Publication No. WO 2013/184572 discloses various crystalline forms of ibrutinib designated as Form A, Form B, Form C, Form D, Form E, and Form F.

PCT Publication No. WO 2015/081180 discloses crystalline Form I of ibrutinib.

Polymorphism, the occurrence of different crystal forms, is a property of some molecules. When polymorphism occurs, the molecules arrange themselves in two or more different ways in the crystal, giving rise to differences in crystal structures and physical properties like melting point, thermal behaviors. X-ray powder diffraction (XRPD) pattern, infra-red absorption (IR) fingerprint, solid state nuclear magnetic resonance spectrum (NMR), and solubility and mechanical properties. Thus, the discovery of new polymorphic forms of a molecule is important in the development of pharmaceuticals, as they may provide materials having desirable processing properties, such as ease of handling, ease of processing, storage stability, ease of purification, improved dissolution profile, and/or improved shelf-life.

SUMMARY OF THE INVENTION

The present invention relates to crystalline forms of ibrutinib, designated as Form S1, Form S2, Form S3, Form S4, and an amorphous form, designated as Form A1, and processes for their preparation, pharmaceutical compositions comprising these forms, and their use for the treatment of Bruton's tyrosine kinase (BTK) mediated diseases.

DETAILED DESCRIPTION OF THE INVENTION

The term "about," as used herein, refers to any value which lies within the range defined by a number up to ±10% of the value.

The term "contacting," as used herein, refers to dissolving, slurrying, stirring, suspending, or combinations thereof.

The term "ambient temperature," as used herein, refers to a temperature in the range of 25° C. to 35° C.

The term "seed crystal," as used herein, refers to a small piece of single crystal/polycrystal material, which is used for addition to a crystallization system for the purpose of initiating or enhancing nucleation or acting as a substrate for further crystallization.

The term "BTK mediated diseases," as used herein, refers to any disease or other deleterious condition in which BTK, or a mutant thereof, is known to play a role. The BTK mediated diseases include autoimmune diseases, heteroimmune conditions or diseases, cancer, and thromboembolic disorders.

The term "dimethoxyethane hemisolvate of ibrutinib," as used herein, refers to a solvate containing one molecule of dimethoxyethane per two molecules of ibrutinib.

A first aspect of the present invention provides a crystalline form of ibrutinib, designated as Form S1, characterized by an XRPD pattern having peaks at d-spacings of about 5.1, 4.5, 4.4, 4.2, and 4.0 Å, and additional peaks at d-spacings of about 13.2, 5.0, 4.1, 3.9, and 3.8 Å.

In an embodiment of this aspect, the crystalline form of ibrutinib, designated as Form S1, is dimethoxyethane hemisolvate of ibrutinib.

Table 1 provides the d-spacing values (Å), the corresponding 2θ values, and the relative intensity of the crystalline form of ibrutinib designated as Form S1.

TABLE 1

| d-spacing (Å) | Position (±0.2° 2θ) | Relative Intensity (%) |
|---|---|---|
| 13.2 | 6.7 | 53.7 |
| 9.1 | 9.7 | 4.9 |
| 8.6 | 10.3 | 29.0 |
| 8.2 | 10.7 | 25.1 |
| 7.2 | 12.4 | 2.7 |
| 6.6 | 13.4 | 28.5 |
| 6.0 | 14.8 | 2.6 |
| 5.8 | 15.4 | 12.6 |
| 5.1 | 17.3 | 100 |
| 5.0 | 17.5 | 48.1 |
| 4.9 | 18.2 | 30.6 |
| 4.8 | 18.5 | 22.6 |
| 4.7 | 18.9 | 23.6 |
| 4.6 | 19.2 | 17.9 |
| 4.5 | 20.0 | 98.3 |
| 4.4 | 20.1 | 79.4 |
| 4.3 | 20.5 | 24.2 |
| 4.2 | 21.4 | 77.2 |
| 4.1 | 21.6 | 45.8 |
| 4.0 | 22.1 | 83.2 |
| 3.9 | 23.0 | 59.4 |
| 3.8 | 23.3 | 74.0 |
| 3.5 | 25.2. | 13.5 |
| 3.4 | 26.3 | 20.1 |
| 3.3 | 26.9 | 28.0 |
| 3.2 | 28.2. | 21.7 |
| 3.1 | 28.6 | 12.4 |
| 3.0 | 29.7 | 20.3 |
| 2.9 | 30.6 | 7.7 |
| 2.8 | 31.2 | 7.8 |
| 2.7 | 33.2 | 5.6 |
| 2.5 | 36.3 | 4.6 |
| 2.4 | 37.9 | 1.7 |
| 2.3 | 39.0 | 4.1 |

The crystalline form of ibrutinib designated as Form S1 is characterized by a DSC thermogram having an endothermic peak at about 102.3° C. and an exothermic peak at about 134.7° C.

Figure 1:
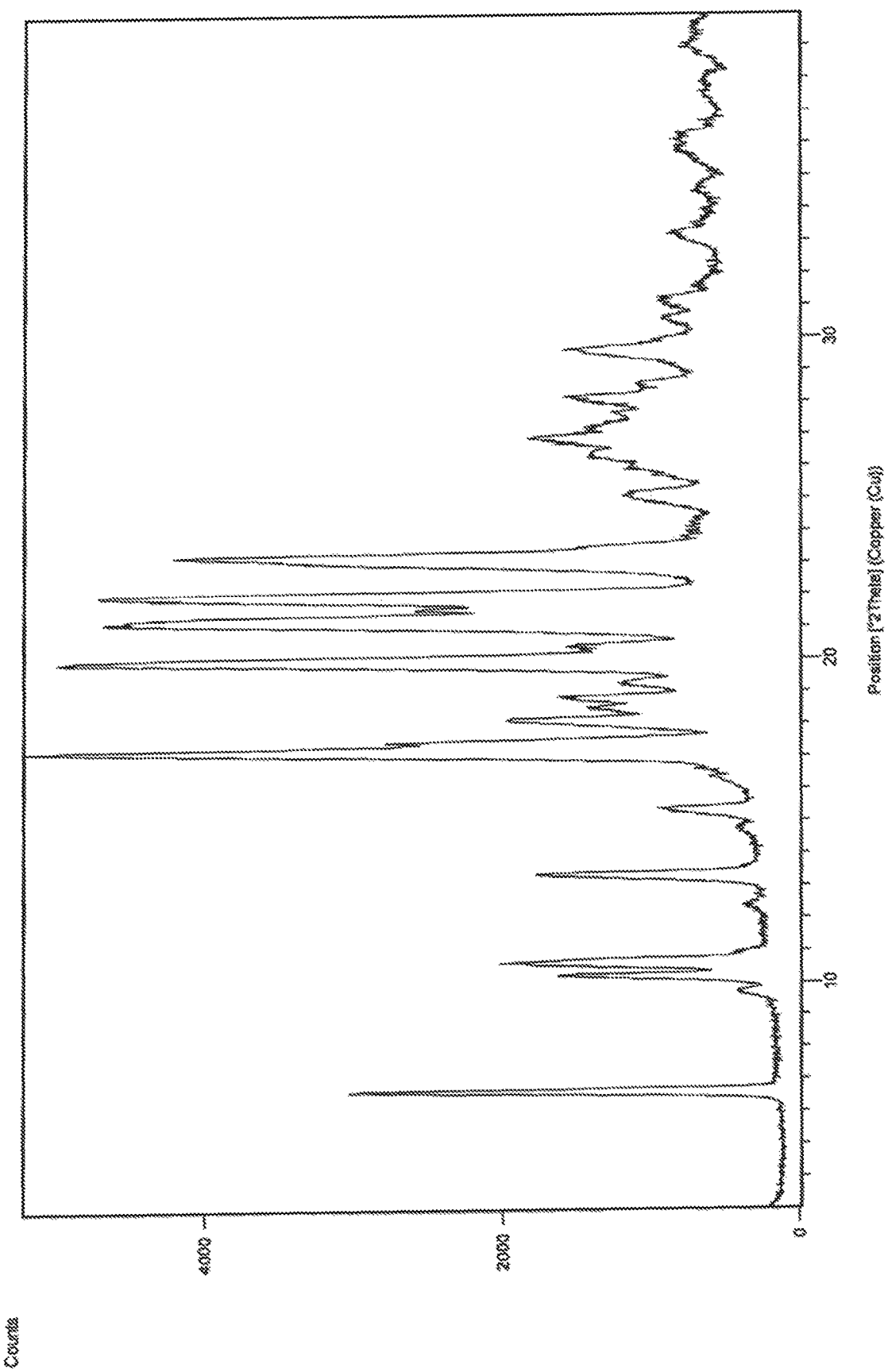
FIG. 1 depicts an X-ray powder diffraction (XRPD) pattern of a crystalline form of ibrutinib, designated as Form S1.
Figure 2:
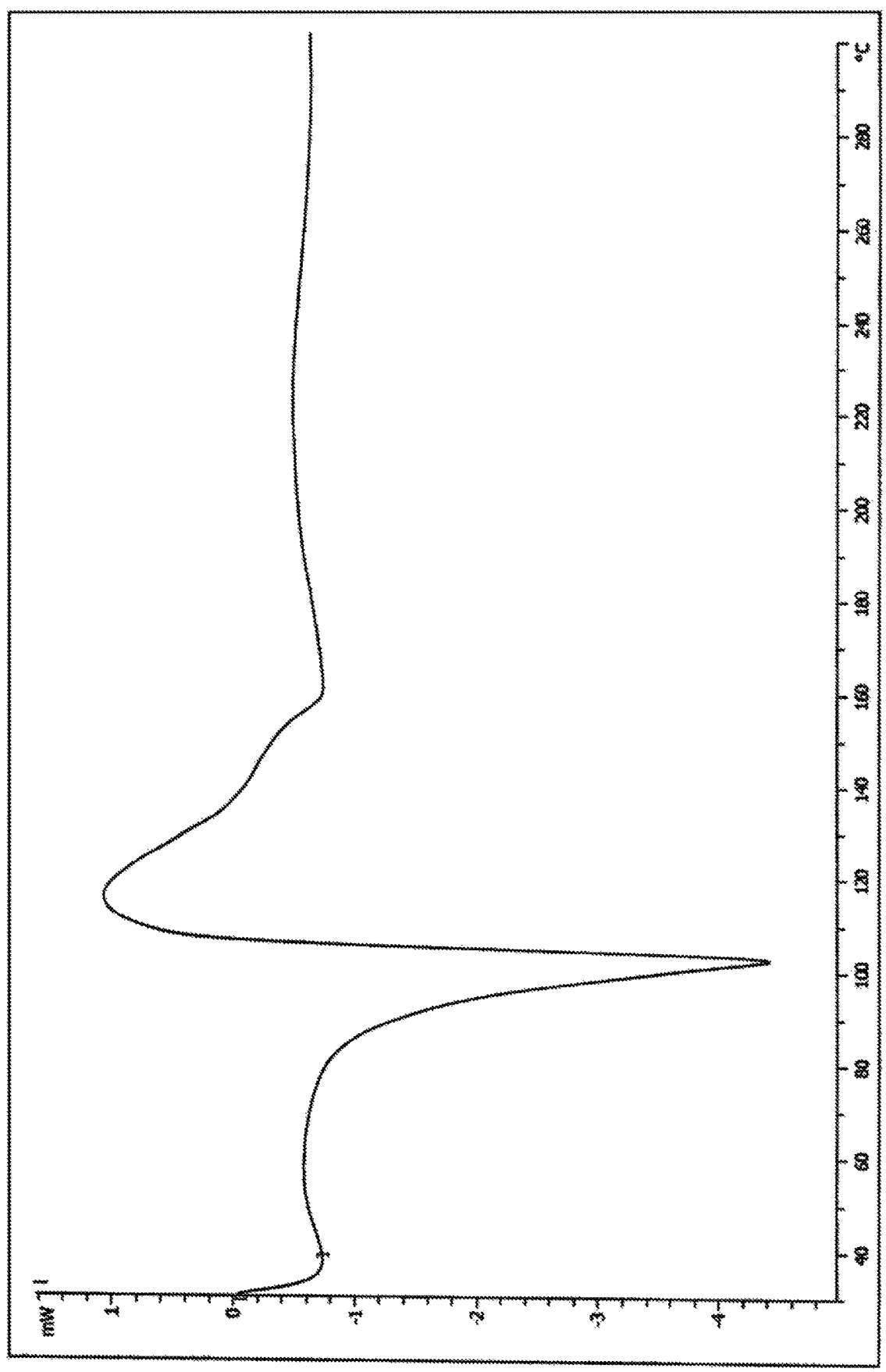
FIG. 2 depicts a Differential Scanning Calorimetry (DSC) thermogram of a crystalline form of ibrutinib, designated as Form S1.
Figure 3:
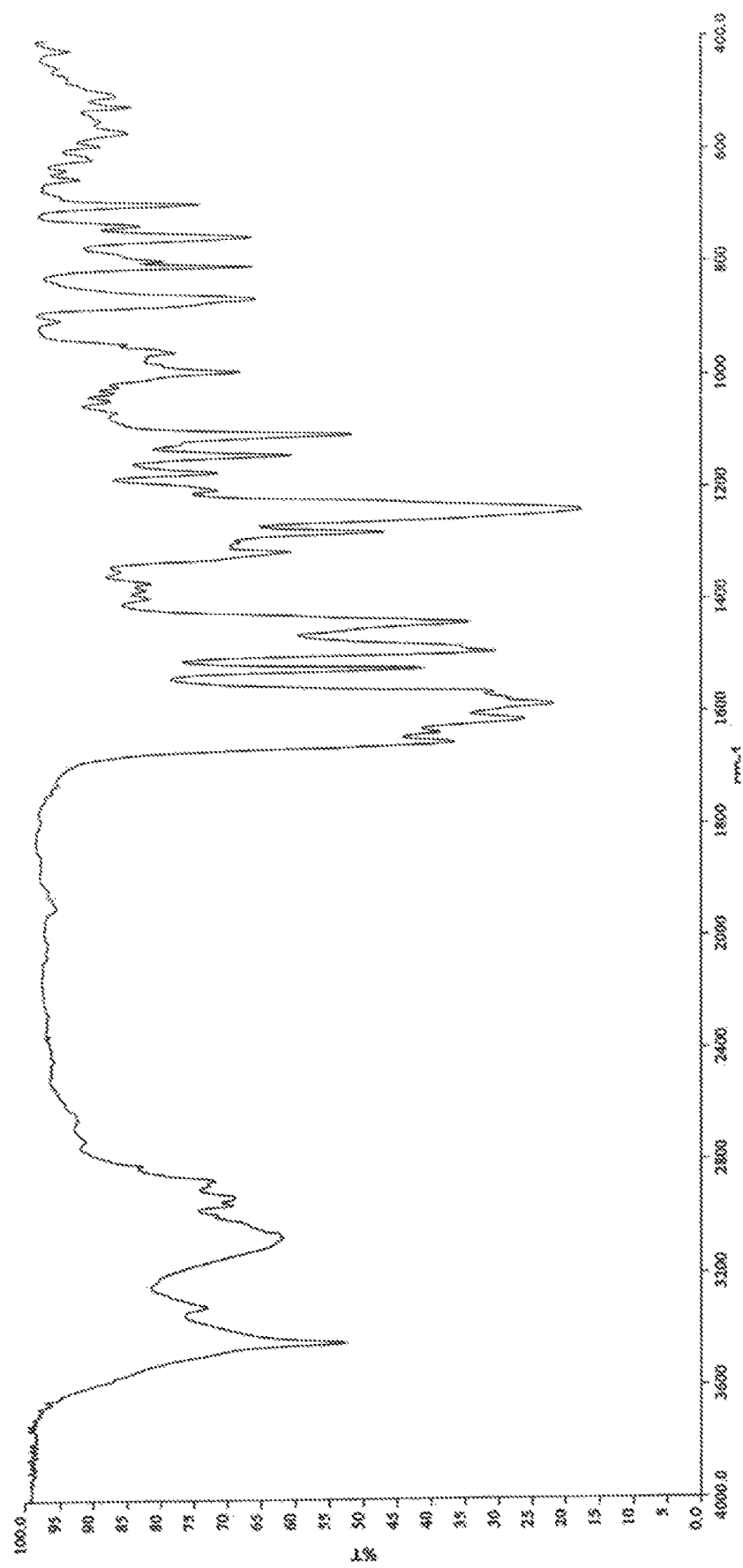
FIG. 3 depicts an Infra-red (IR) spectrum of a crystalline form of ibrutinib, designated as Form S1.

The crystalline form of ibrutinib designated as Form S1 is also characterized by an XRPD pattern substantially as depicted in FIG. 1, a DSC thermogram substantially as depicted in FIG. 2, or an IR absorption spectrum substantially as depicted in FIG. 3.

A second aspect of the present invention provides a process for the preparation of a crystalline form of ibrutinib designated as Form S1 comprising contacting ibrutinib with dimethoxyethane, optionally in the presence of an anti-solvent.

Ibrutinib used for the preparation of the crystalline form of ibrutinib designated as Form S1 can be prepared by following the methods as described in the art, for example, in U.S. Pat. No. 7,514,444 or PCT Publication No. WO 2013/184572.

The anti-solvent used for the preparation of the crystalline form of ibrutinib designated as Form S1 is selected from the group consisting of heptane, hexane, cyclohexane, methylcyclohexane, and diisopropylether.

The preparation of the crystalline form of ibrutinib designated as Form S1 is carried out at a temperature of about −15° C. to about 35° C., for example, at about −10° C. to about 30° C.

The preparation of the crystalline form of ibrutinib designated as Form S1 is carried out for about 15 minutes to about 24 hours, for example, for about 1 hour to about 10 hours.

The crystalline form of ibrutinib designated as Form S1 may be isolated by filtration, decantation, extraction, distillation, evaporation, chromatography, precipitation, concentration, crystallization, centrifugation, or recrystallization, and dried under reduced pressure, by air drying, or by vacuum tray drying.

A third aspect of the present invention provides a crystalline form of ibrutinib, designated as Form S2, characterized by an XRPD pattern having peaks at d-spacings of about 13.1, 5.0, 4.7, 4.1, and 4.0 Å, and additional peaks at d-spacings of about 8.5, 4.5, 4.3, 3.9, and 3.8 Å.

Table 2 provides the d-spacing values (Å), the corresponding 2θ values, and the relative intensity of the crystalline form of ibrutinib designated as Form S2.

TABLE 2

| d-spacing (Å) | Position (±0.2° 2θ) | Relative Intensity (%) |
|---|---|---|
| 13.1 | 6.7 | 100 |
| 8.9 | 10.0 | 10.5 |
| 8.5 | 10.4 | 21.2 |
| 8.0 | 11.0 | 14.3 |
| 7.3 | 12.1 | 3.4 |
| 6.9 | 12.9 | 5.7 |
| 6.6 | 13.5 | 11.6 |
| 5.8 | 15.3 | 6.2 |
| 5.5 | 16.0 | 9.6 |
| 5.3 | 16.7 | 18.2 |
| 5.0 | 17.6 | 38.0 |
| 4.7 | 18.7 | 40.0 |
| 4.5 | 19.8 | 25.4 |
| 4.3 | 20.9 | 32.4 |
| 4.1 | 71.5 | 42.0 |
| 4.0 | 22.2 | 37.7 |
| 3.9 | 22.5 | 30.4 |
| 3.8 | 23.2 | 21.1 |
| 3.7 | 24.4 | 4.9 |
| 3.5 | 25.8 | 5.2 |
| 2.5 | 35.7 | 2.3 |

The crystalline form of ibrutinib designated as Form S2 is characterized by a DSC thermogram having an endothermic peak at about 89.9° C. and an exothermic peak at about 138.7° C.

Figure 4:
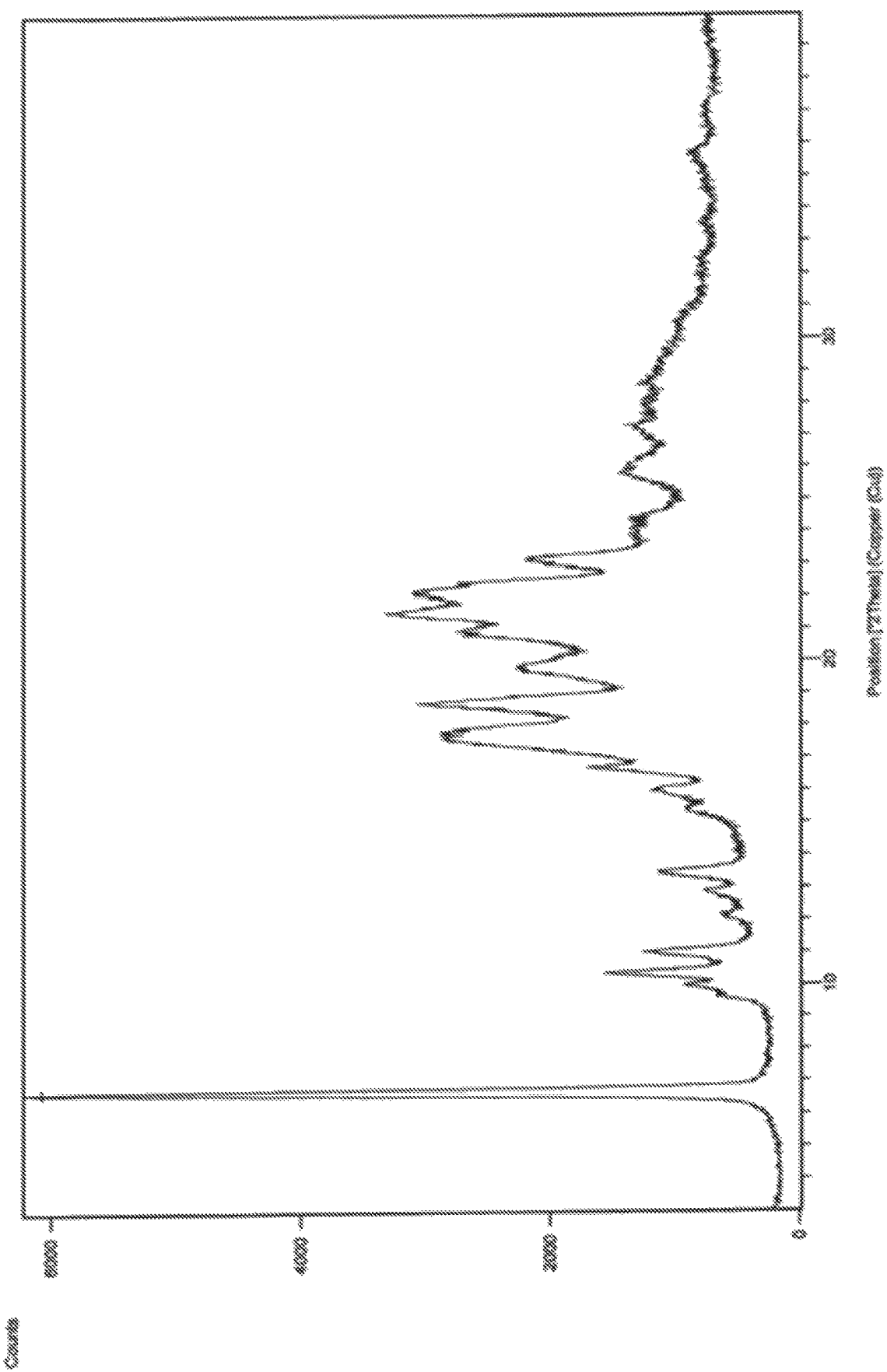
FIG. 4 depicts an XRPD pattern of a crystalline form of ibrutinib, designated as Form S2.
Figure 5:
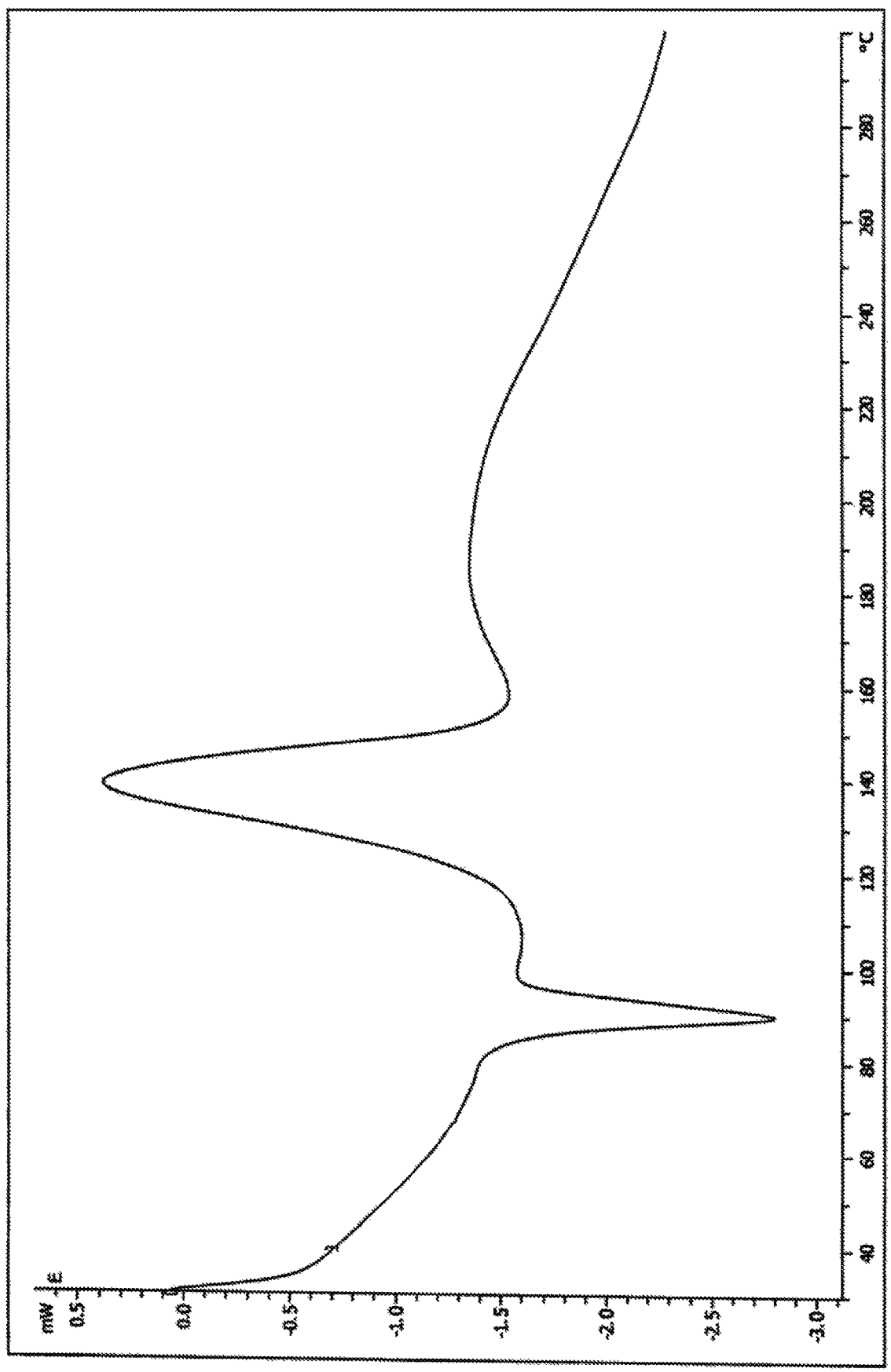
FIG. 5 depicts a DSC thermogram of a crystalline form of ibrutinib, designated as Form S2.
Figure 6:
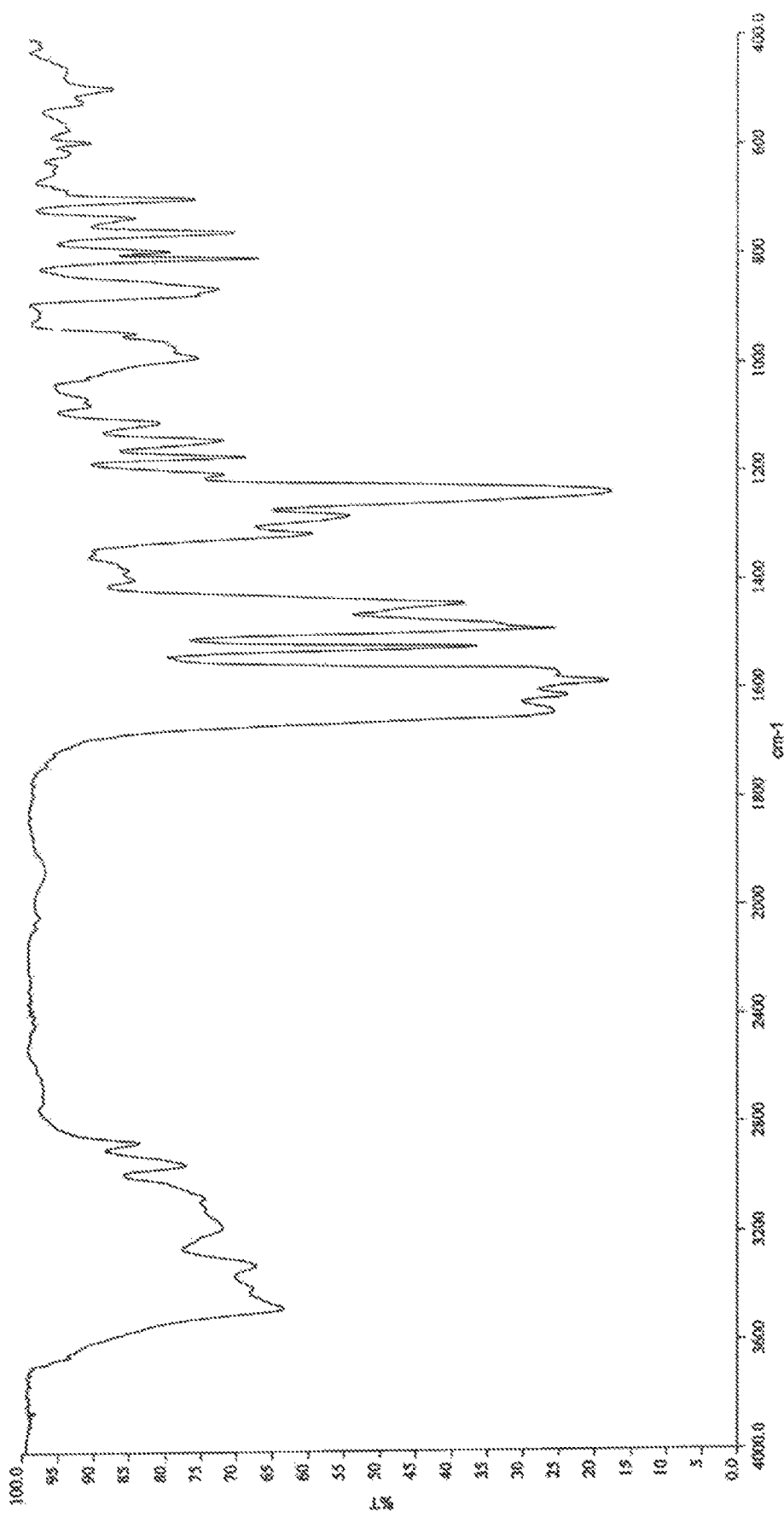
FIG. 6 depicts an IR spectrum of a crystalline form of ibrutinib, designated as Form S2.

The crystalline form of ibrutinib designated as Form S2 is also characterized by an XRPD pattern substantially as depicted in FIG. 4, a DSC thermogram substantially as depicted in FIG. 5, or an IR absorption spectrum substantially as depicted in FIG. 6.

A fourth aspect of the present invention provides a process for the preparation of a crystalline form of ibrutinib designated as Form S2, comprising drying a crystalline form of ibrutinib, designated as Form S1, at about 30° C. to about 60° C.

The preparation of the crystalline form of ibrutinib designated as Form S2 is carried out at about 35° C. to about 55° C.

The preparation of the crystalline form of ibrutinib designated as Form S2 is carried out for about 35 hours to about 55 hours, for example, for about 40 hours to about 50 hours.

The crystalline form of ibrutinib designated as Form S2 may be dried under reduced pressure or by vacuum tray drying.

A fifth aspect of the present invention provides a crystalline form, designated as Form S3 of ibrutinib, characterized by an XRPD pattern having peaks at d-spacings of about 14.0, 4.7, 4.4, 4.2, and 3.9 Å, and additional peaks at d-spacings of about 8.3, 7.4, 5.7, 5.3, and 4.9 Å.

Table 3 provides the d-spacing values (Å), the corresponding 2θ values, and the relative intensity of the crystalline form of ibrutinib designated as Form S3.

TABLE 3

| d-spacing (Å) | Position (±0.2° 2θ) | Relative Intensity (%) |
|---|---|---|
| 16.5 | 5.4 | 5.6 |
| 14.0 | 6.3 | 100 |
| 8.3 | 10.6 | 37.9 |
| 8.0 | 11.0 | 16.8 |
| 7.4 | 12.0 | 18.2 |
| 6.7 | 13.2 | 13.1 |
| 5.7 | 15.7 | 34.5 |
| 5.3 | 16.7 | 28.3 |
| 4.9 | 18.2 | 57.3 |
| 4.7 | 19.0 | 80.5 |
| 4.4 | 20.2 | 93.0 |
| 4.2 | 21.4 | 73.2 |
| 3.9 | 23.1 | 71.2 |
| 3.0 | 29.3 | 5.4 |

The crystalline form of ibrutinib designated as Form S3 is characterized by a DSC thermogram having endothermic peaks at about 65.3° C., 92.7° C., 98.2° C., 117.2° C., 136.2° C., and 144.8° C.

Figure 7:
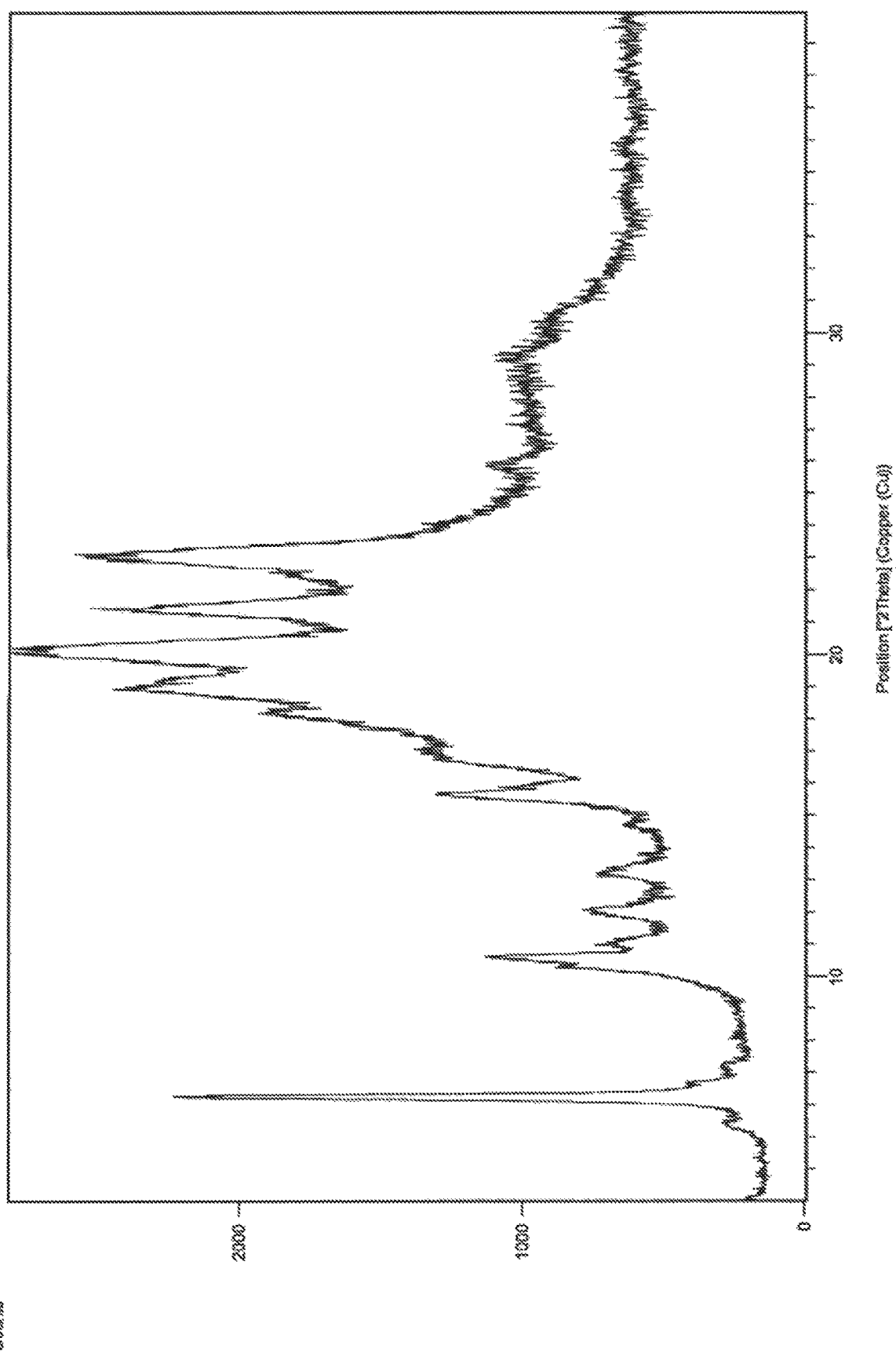
FIG. 7 depicts an XRPD pattern of a crystalline form of ibrutinib, designated as Form S3.
Figure 8:
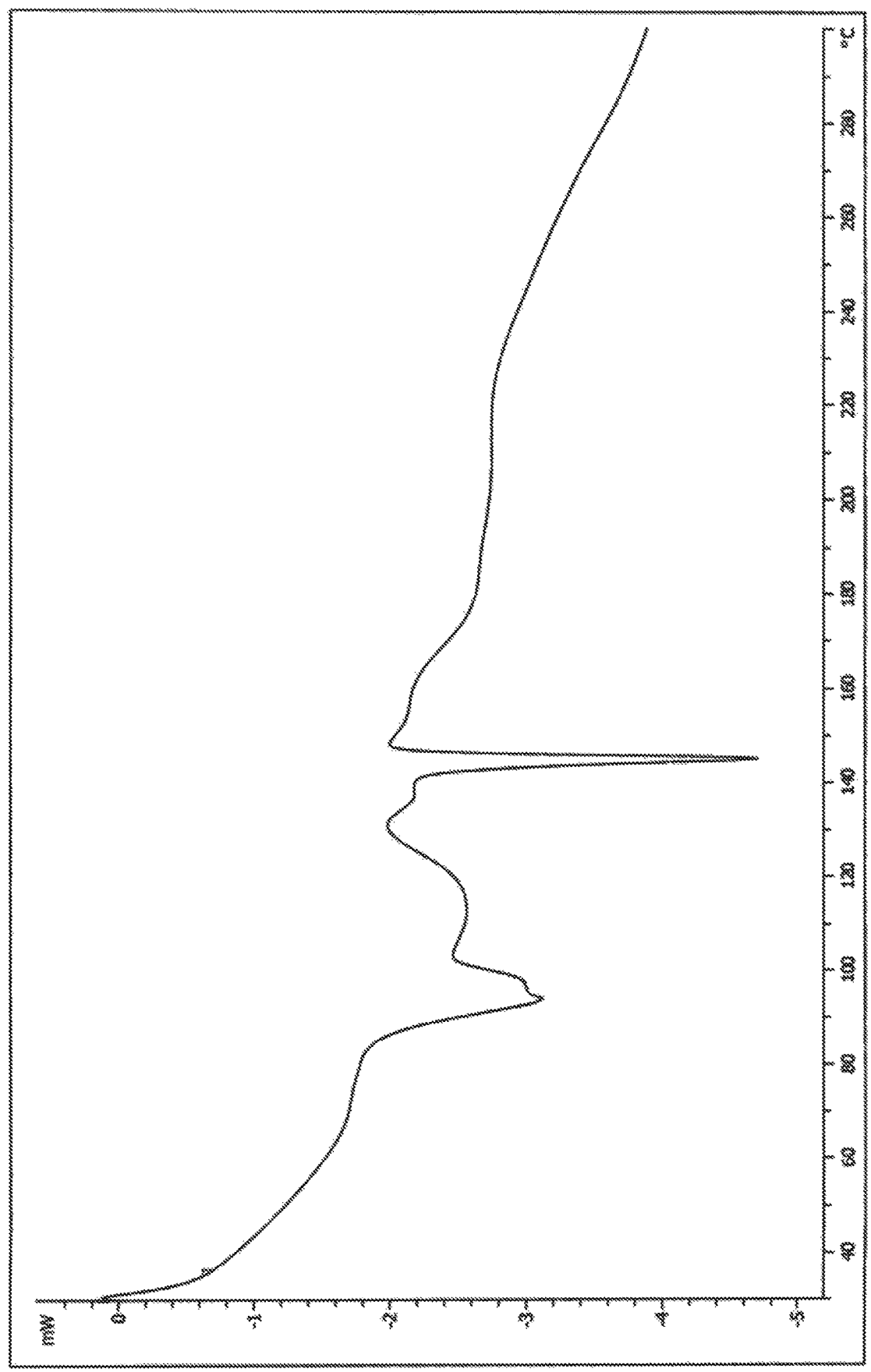
FIG. 8 depicts a DSC thermogram of a crystalline form of ibrutinib, designated as Form S3.
Figure 9:
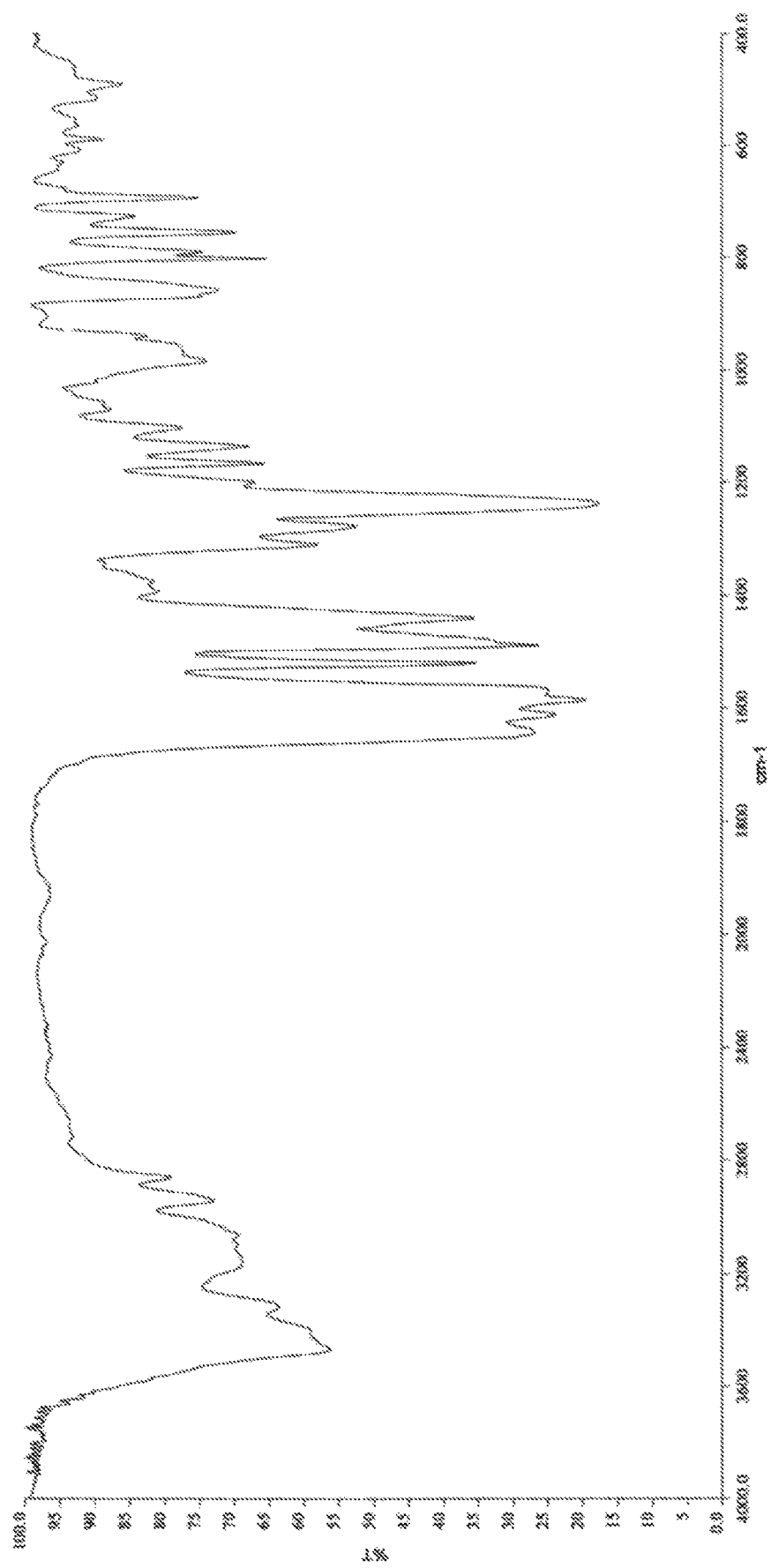
FIG. 9 depicts an IR spectrum of a crystalline form of ibrutinib, designated as Form S3.

The crystalline form of ibrutinib designated as Form S3 is also characterized by an XRPD pattern substantially as depicted in FIG. 7, a DSC thermogram substantially as depicted in FIG. 8, or an IR absorption spectrum substantially as depicted in FIG. 9.

A sixth aspect of the present invention provides a process for the preparation of a crystalline form of ibrutinib, designated as Form S3, comprising drying a crystalline form of ibrutinib designated as Form S1 at about 70° C.

The preparation of the crystalline form of ibrutinib designated as Form S3 is carried out for about 5 hours to about 15 hours, for example, for about 8 hours to about 10 hours.

The crystalline form of ibrutinib designated as Form S3 may be dried under reduced pressure or by vacuum tray drying.

A seventh aspect of the present invention provides an amorphous form of ibrutinib, designated as Form A1.

The amorphous form of ibrutinib designated as Form A1 is characterized by a DSC thermogram having endothermic peaks at about 67.8° C., 107.9° C., 134.6° C., and 144.9° C.

Figure 10:
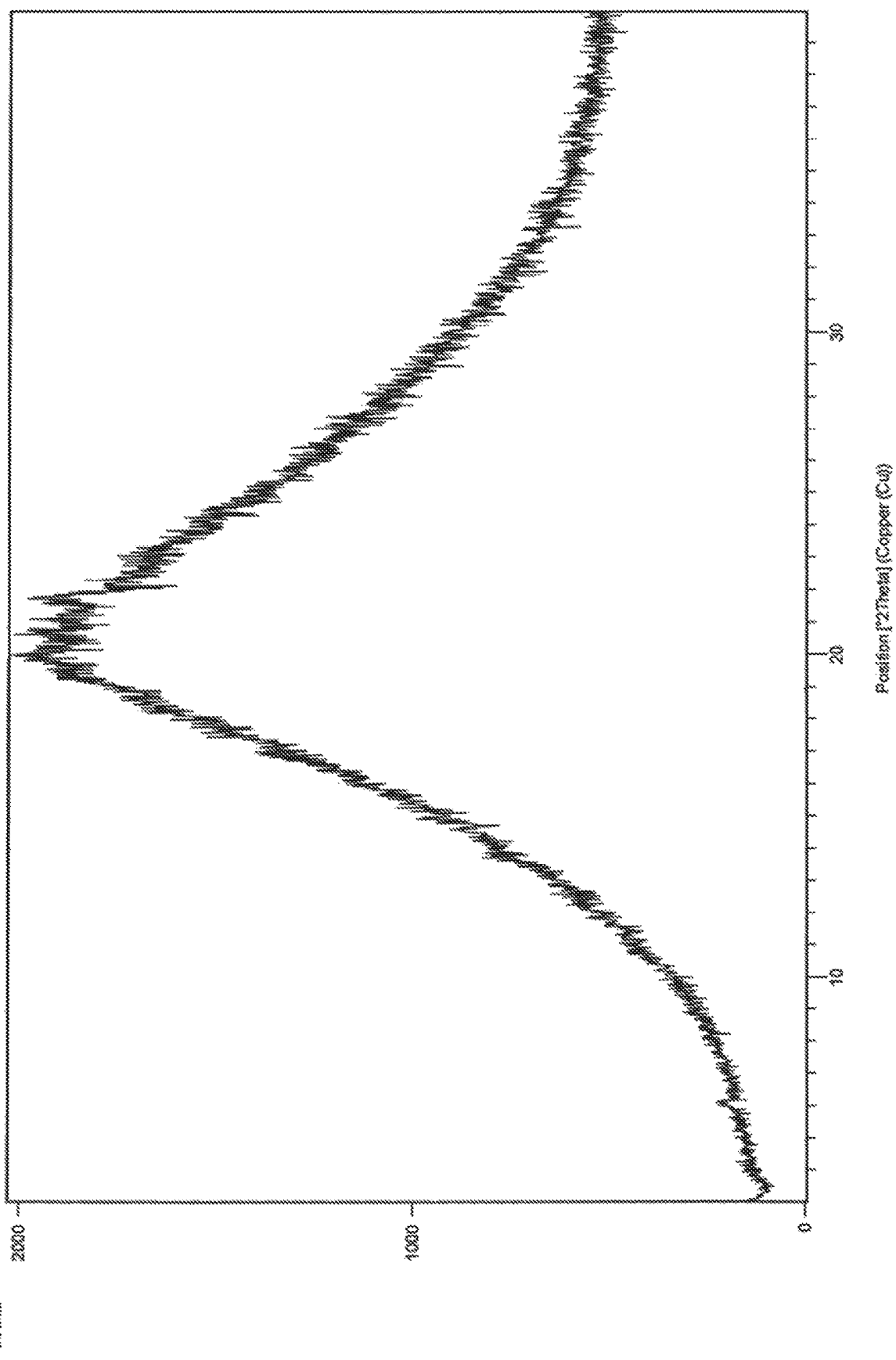
FIG. 10 depicts an XRPD pattern of an amorphous form of ibrutinib, designated as Form A1.
Figure 11:
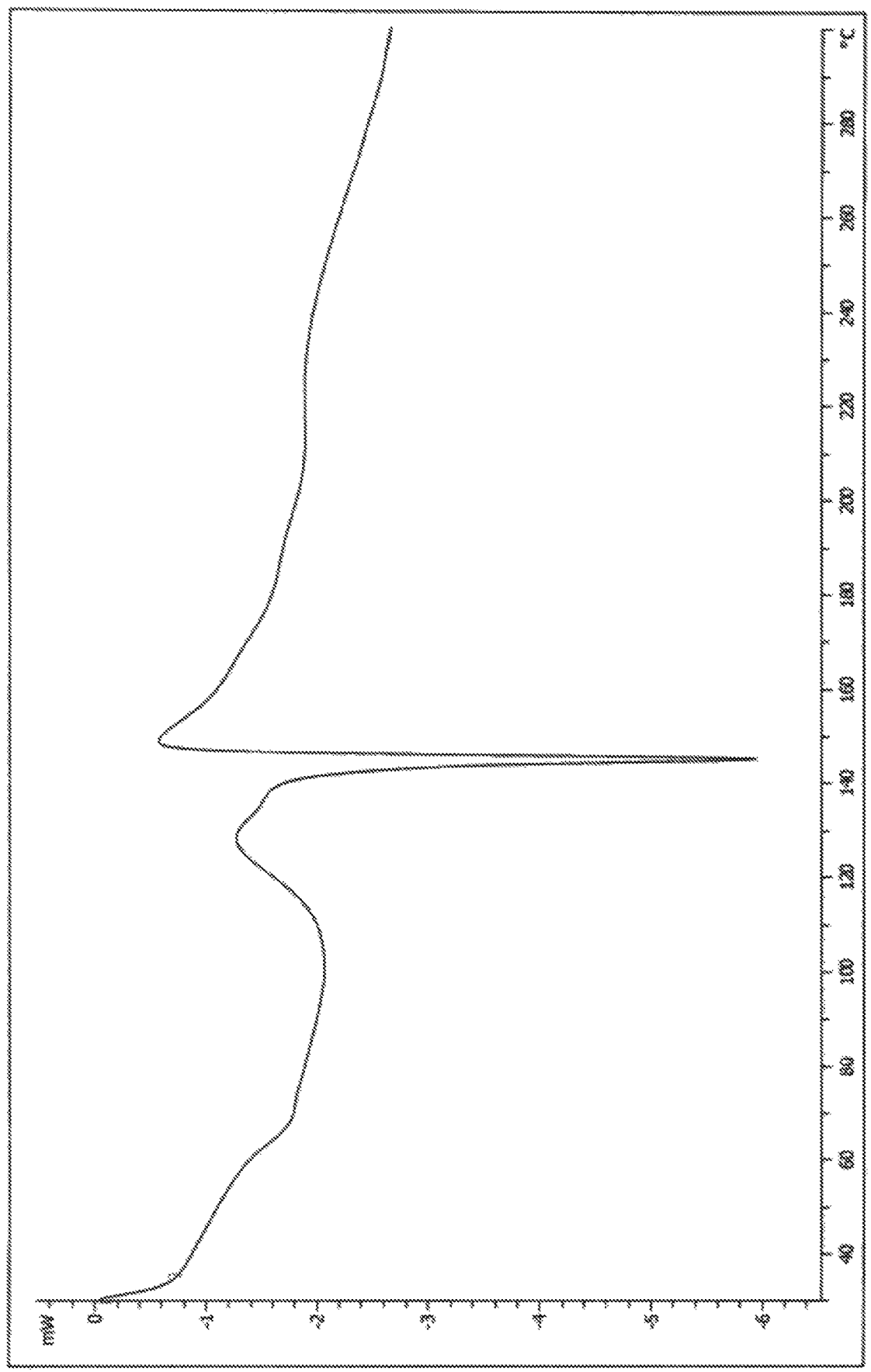
FIG. 11 depicts a DSC thermogram of an amorphous form of ibrutinib, designated as Form A1.
Figure 12:
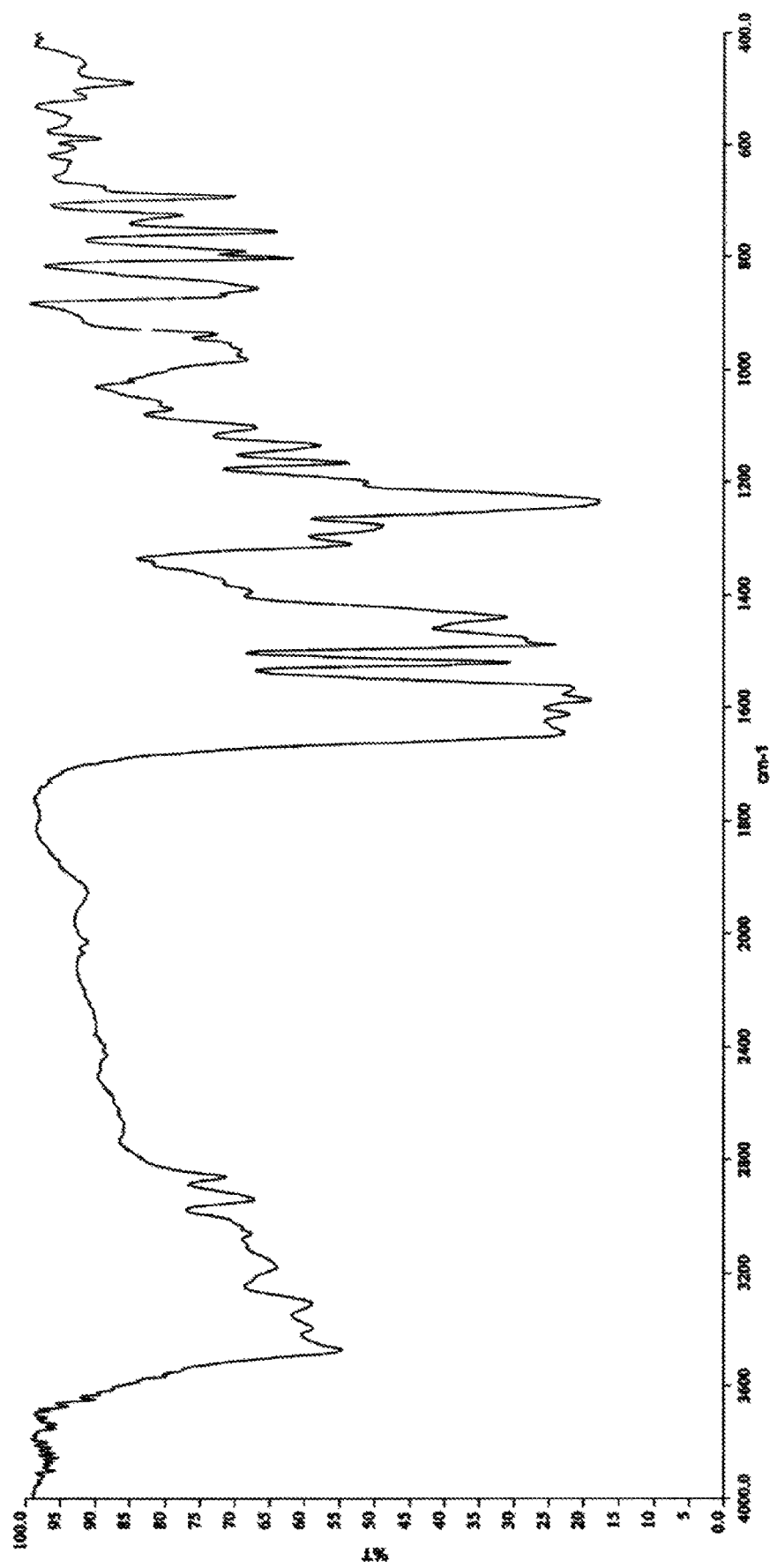
FIG. 12 depicts an IR spectrum of an amorphous form of ibrutinib, designated as Form A1.

The amorphous form of ibrutinib designated as Form A1 is characterized by an XRPD pattern substantially as depicted in FIG. 10, a DSC thermogram substantially as depicted in FIG. 11, or an IR absorption spectrum substantially as depicted in FIG. 12.

An eighth aspect of the present invention provides a process for the preparation of an amorphous form of ibrutinib designated as Form A1, comprising drying a crystalline form of ibrutinib designated as Form S3 at about 90° C.

The preparation of the amorphous form of ibrutinib designated as Form A1 is carried out for about 30 minutes to about 5 hours, for example, for about one hour to about 3 hours.

The amorphous form of ibrutinib designated as Form A1 may be dried under reduced pressure or by vacuum tray drying.

A ninth aspect of the present invention provides a crystalline form of ibrutinib, designated as Form S4, characterized by an XRPD pattern having peaks at d-spacings of about 14.7 and 4.2 Å, and additional peaks at d-spacings of about 7.5, 7.3, 6.4, 3.8, and 3.7 Å.

Table 4 provides the d-spacing values (Å), the corresponding 2θ values, and the relative intensity of the crystalline form of ibrutinib designated as Form S4.

TABLE 4

| d-spacing (Å) | Position (±0.2° 2θ) | Relative Intensity (%) |
|---|---|---|
| 14.7 | 6.0 | 54.5 |
| 8.7 | 10.1 | 13.1 |
| 8.5 | 10.4 | 26.5 |
| 8.4 | 10.6 | 21.3 |
| 8.2 | 10.8 | 28.9 |
| 7.5 | 11.8 | 12.1 |
| 7.3 | 12.1 | 19.6 |
| 6.8 | 13.0 | 4.5 |
| 6.5 | 13.6 | 24.5 |
| 6.4 | 13.8 | 17.4 |
| 5.6 | 15.8 | 23.4 |
| 5.5 | 16.0 | 18.7 |
| 5.3 | 16.7 | 31.2 |
| 5.1 | 17.3 | 15.1 |
| 4.9 | 18.1 | 79.0 |
| 4.8 | 18.4 | 31.8 |
| 4.6 | 19.2 | 44.2 |
| 4.5 | 19.4 | 48.5 |
| 4.4 | 19.8 | 89.0 |
| 4.3 | 20.5 | 42.7 |
| 4.2 | 20.9 | 55.9 |
| 4.1 | 21.6 | 100 |
| 4.0 | 22.4 | 22.8 |
| 3.9 | 22.9 | 32.6 |
| 3.8 | 23.2 | 24.4 |
| 3.7 | 23.7 | 20.0 |
| 3.6 | 24.5 | 12.4 |
| 3.5 | 25.0 | 8.4 |
| 3.4 | 26.4 | 10.8 |
| 3.3 | 26.8 | 14.5 |
| 3.2 | 27.8 | 8.0 |
| 3.1 | 28.7 | 9.2 |
| 3.0 | 29.5 | 10.8 |
| 2.9 | 30.8 | 9.5 |
| 2.8 | 32.2 | 6.2 |
| 2.6 | 33.9 | 1.3 |
| 2.5 | 35.2 | 1.7 |

The crystalline form of ibrutinib designated as Form S4 is characterized by a DSC thermogram having an endothermic peak at about 145° C.

Figure 13:
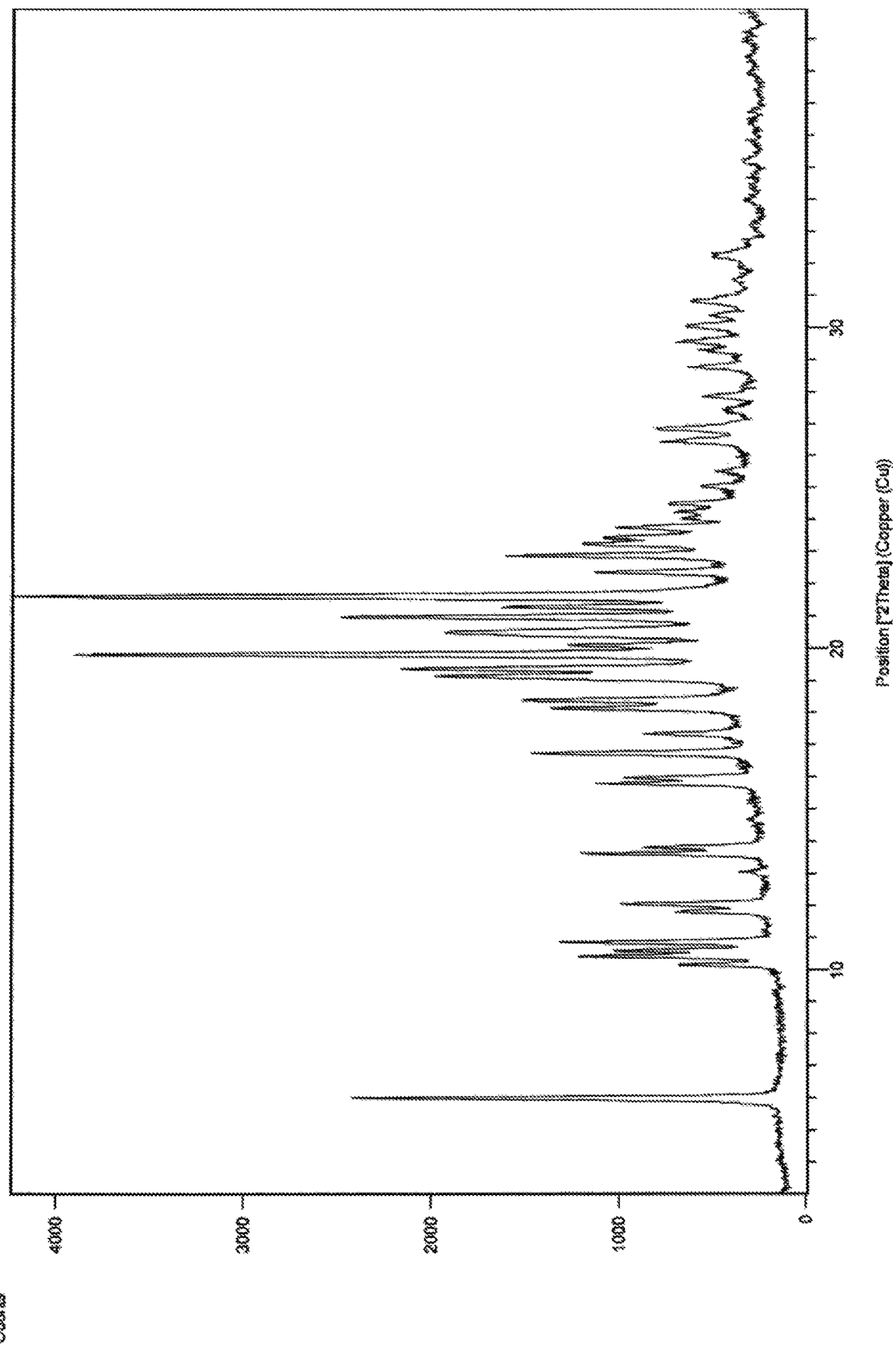
FIG. 13 depicts an XRPD pattern of a crystalline form of ibrutinib, designated as Form S4.
Figure 14:
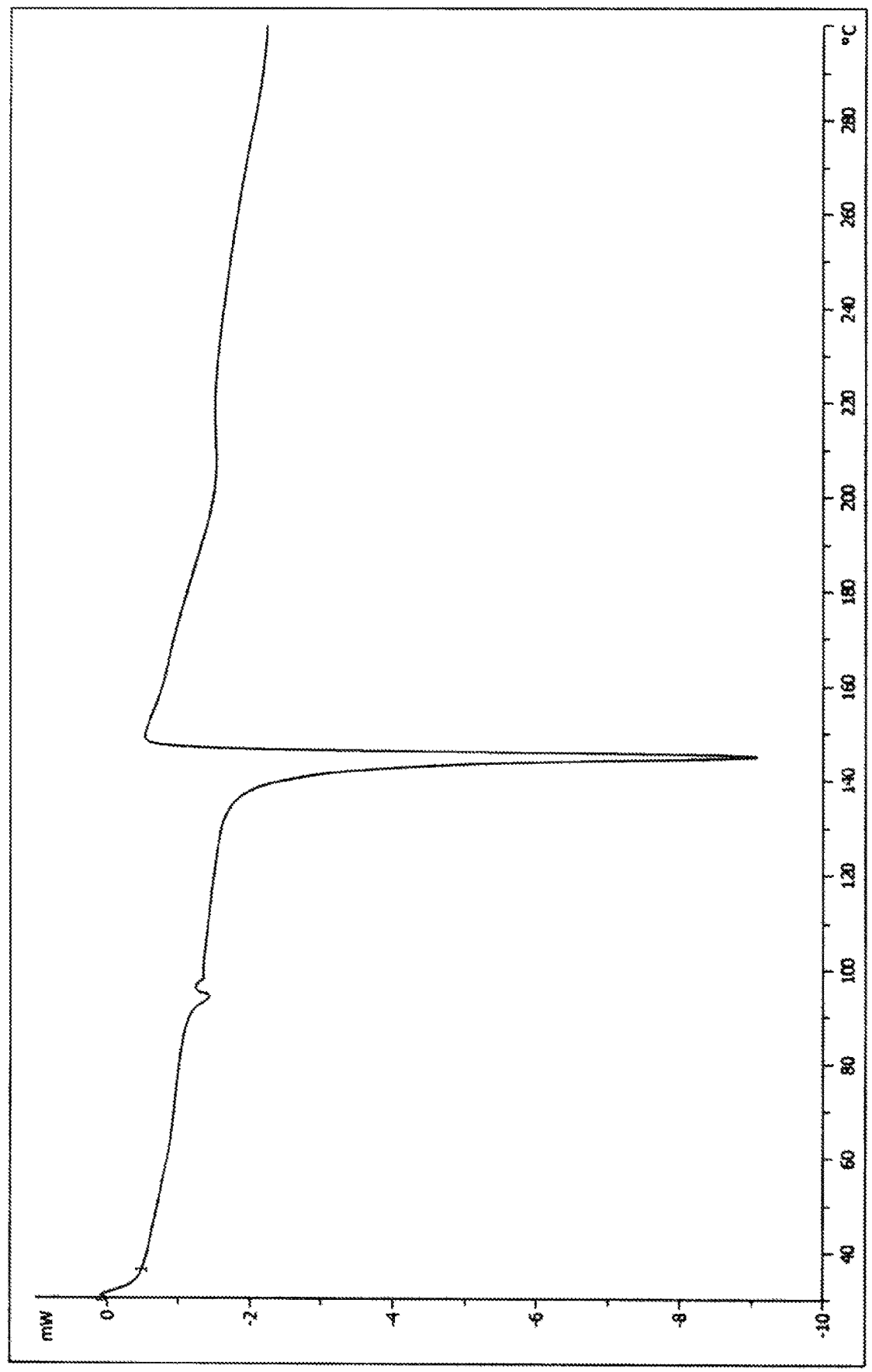
FIG. 14 depicts a DSC thermogram of a crystalline form of ibrutinib, designated as Form S4.
Figure 15:
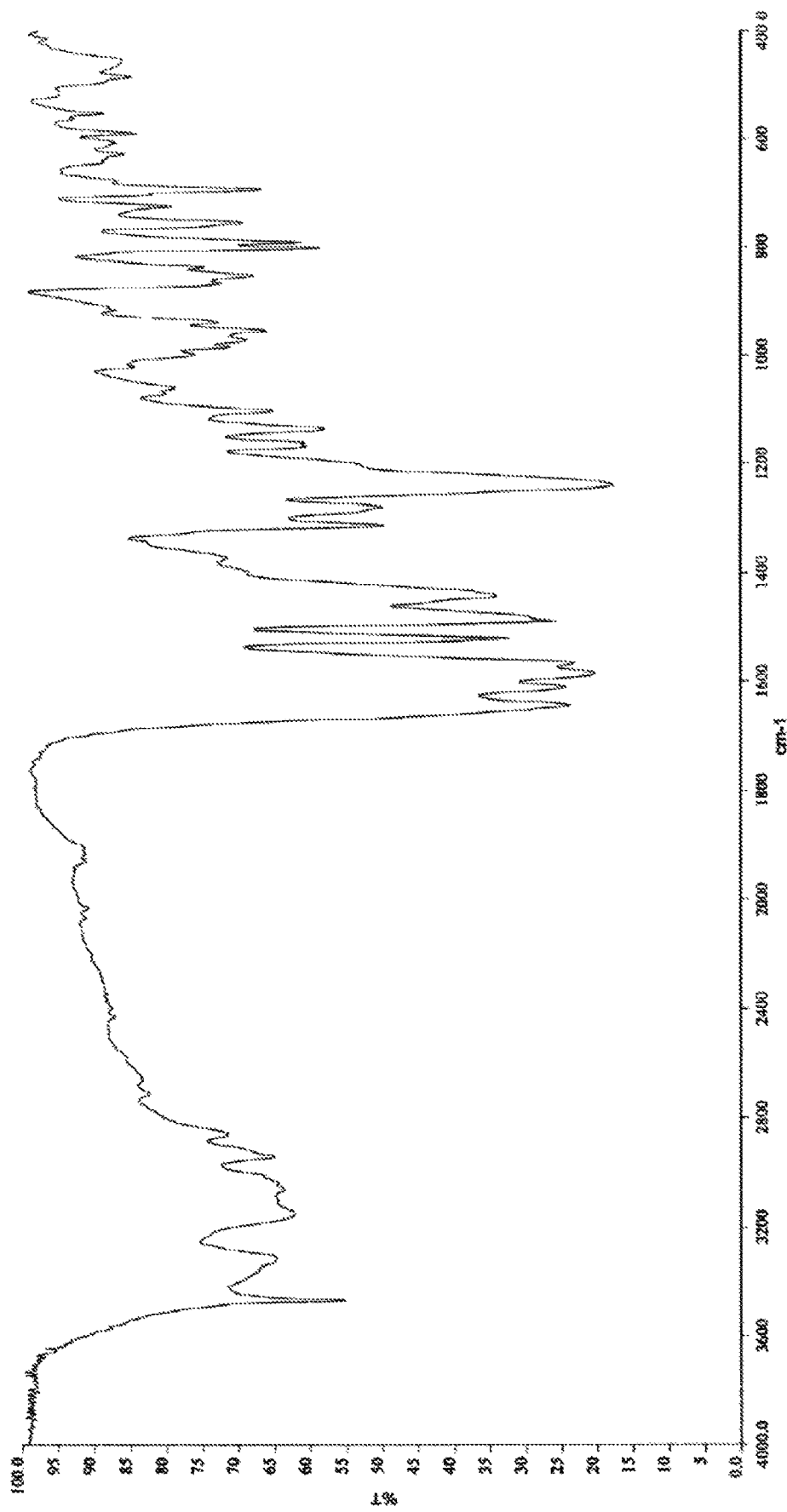
FIG. 15 depicts an IR spectrum of a crystalline form of ibrutinib, designated as Form S4.
Figure 16:
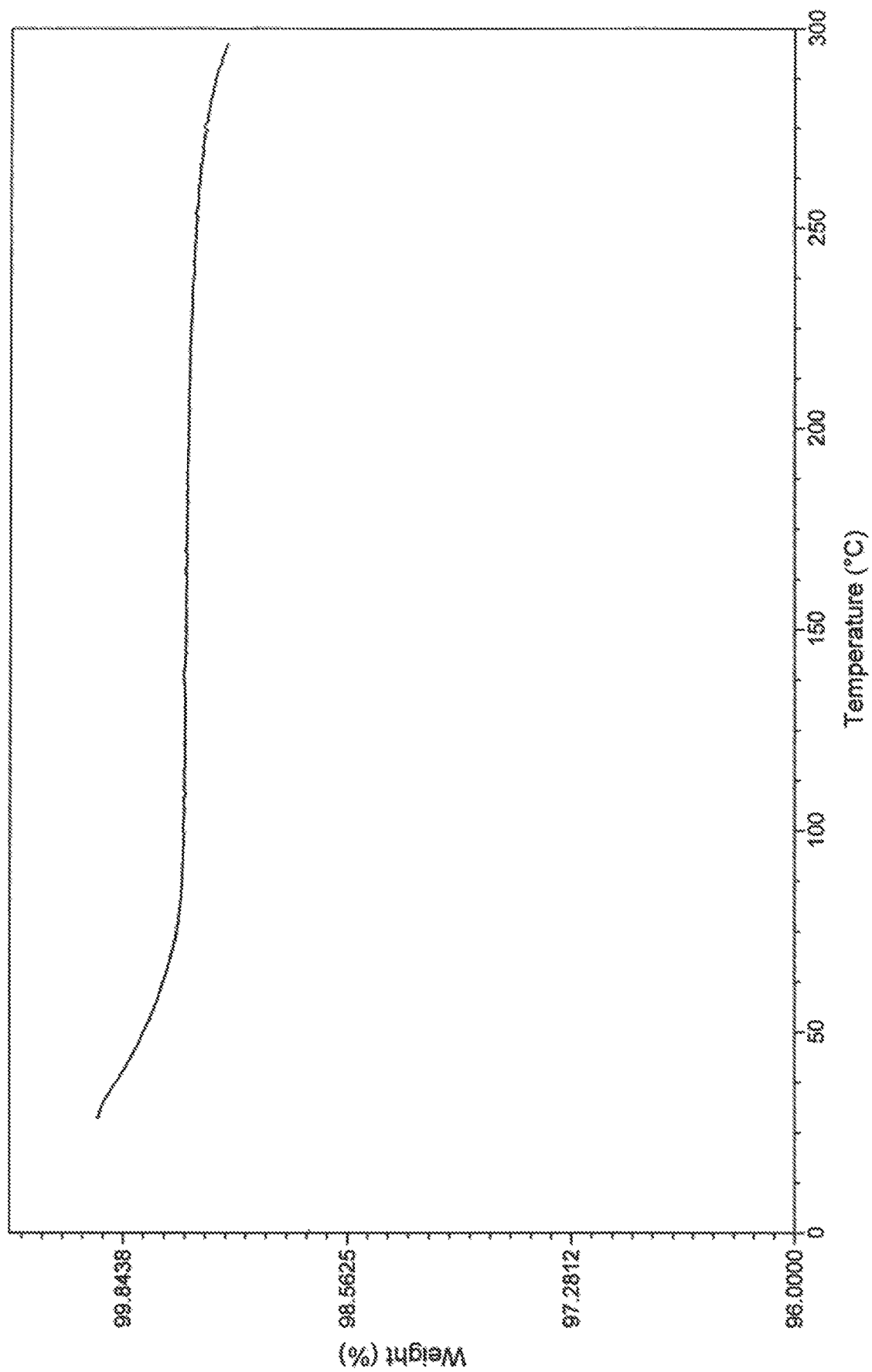
FIG. 16 depicts a Thermogravimetric Analysis (TGA) thermogram of a crystalline form of ibrutinib, designated as Form S4.

The crystalline form of ibrutinib designated as Form S4 is also characterized by an XRPD pattern substantially as depicted in FIG. 13, a DSC thermogram substantially as depicted in FIG. 14, an IR absorption spectrum substantially as depicted in FIG. 15, or a TGA thermogram substantially as depicted in FIG. 16.

A tenth aspect of the present invention provides a process for the preparation of a crystalline form of ibrutinib designated as Form S4, comprising drying a crystalline form of ibrutinib, designated as Form S3.

The preparation of the crystalline form of ibrutinib designated as Form S4 is carried out for about 30 minutes to about 5 hours, for example, for about 1 hour to about 3 hours.

The preparation of the crystalline form of ibrutinib designated as Form S4 is carried out at a temperature of about 80° C. to about 160° C., for example, at about 100° C. to about 140° C.

The crystalline form of ibrutinib designated as Form S4 may be dried under reduced pressure or by vacuum tray drying.

An eleventh aspect of the present invention provides a process for the preparation of a crystalline form of ibrutinib designated as Form S4, comprising drying an amorphous form of ibrutinib designated as Form A1.

The preparation of the crystalline form of ibrutinib designated as Form S4 is carried out for about 30 minutes to about 5 hours, for example, for about 1 hour to about 3 hours.

The preparation of the crystalline form of ibrutinib designated as Form S4 is carried out at a temperature of about 80° C. to about 160° C., for example, at about 100° C. to about 140° C.

The crystalline form of ibrutinib designated as Form S4 may be dried under reduced pressure or by vacuum tray drying.

A twelfth aspect of the present invention provides a process for the preparation of a crystalline form of ibrutinib designated as Form S4, comprising:
  a) seeding a crystalline form of ibrutinib designated as Form S1, with the seed crystals of a crystalline form of ibrutinib, designated as Form S4; and
  b) drying the mixture of step a) to obtain the crystalline form of ibrutinib designated as Form S4.

The preparation of the crystalline form of ibrutinib designated as Form S4 is carried out at a temperature of about 70° C. to about 140° C., for example, at about 80° C. to about 130° C.

The preparation of the crystalline form of ibrutinib designated as Form S4 is carried out for about 30 minutes to about 8 hours, for example, for about 1 hour to about 6 hours.

The crystalline form of ibrutinib designated as Form S4 may be dried under reduced pressure or by vacuum tray drying.

A thirteenth aspect of the present invention provides a process for the preparation of a crystalline form of ibrutinib designated as Form S4, comprising:
  a) seeding an amorphous form of ibrutinib designated as Form A1, with the seed crystals of a crystalline form of ibrutinib designated as Form S4; and
  b) drying the mixture of step a) to obtain the crystalline form of ibrutinib designated as Form S4.

The preparation of the crystalline form of ibrutinib designated as Form S4 is carried out at a temperature of about 90° C. to about 140° C., for example, at about 100° C. to about 130° C.

The preparation of the crystalline form of ibrutinib designated as Form S4 is carried out for about 1 hour to about 4 hours, for example, for about 2 hours to about 3 hours.

The crystalline form of ibrutinib designated as Form S4 may be dried under reduced pressure or by vacuum tray drying.

A fourteenth aspect of the present invention provides a process for the preparation of a crystalline form of ibrutinib designated as Form S4 comprising:
  a) contacting ibrutinib with a halogenated hydrocarbon; and
  b) adding the seed crystals of a crystalline form of ibrutinib designated as Form S4 to obtain the crystalline form of ibrutinib designated as Form S4.

Ibrutinib used for the preparation of the crystalline form of ibrutinib designated as Form S4 can be prepared by following the methods as described in the art, for example, in U.S. Pat. No. 7,514,444 or PCT Publication No. WO 2013/184572.

The halogenated hydrocarbon is selected from the group consisting of dichloromethane, dichloroethane, and chloroform.

The preparation of the crystalline form of ibrutinib designated as Form S4 is carried out at a temperature of about 20° C. to about 90° C., for example, at about 25° C. to about 80° C.

The preparation of the crystalline form of ibrutinib, designated as Form S4 is carried out for about 1 hour to about 30 hours, for example, for about 2 hours to about 25 hours.

The crystalline form of ibrutinib designated as Form S4 may be isolated by filtration, decantation, extraction, distillation, evaporation, chromatography, precipitation, concentration, crystallization, centrifugation, or recrystallization, and dried under reduced pressure, by air drying, or by vacuum tray drying.

A fifteenth aspect of the present invention provides a pharmaceutical composition comprising crystalline forms selected from the group consisting of Form S1, Form S2, Form S3, and Form S4, and amorphous Form A1 of ibrutinib, and one or more pharmaceutically acceptable carriers, diluents, or excipients.

A sixteenth aspect of the present invention provides a method for treating Bruton's tyrosine kinase (BTK) mediated diseases comprising administering to a patient in need thereof a therapeutically effective amount of a composition comprising crystalline forms selected from the group consisting of Form S1, Form S2, Form S3, and Form S4, and amorphous Form A1 of ibrutinib.

While the present invention has been described in terms of its specific aspects and embodiments, certain modifications and equivalents will be apparent to those skilled in the art, and are intended to be included within the scope of the present invention.

Methods

XRPD of the samples was determined by using a PANalytical® instrument; Model X'pert PRO; Detector: X'celerator®.

IR of the samples was recorded using a PerkinElmer® instrument, potassium bromide pellet method.

DSC of the samples was recorded using a Mettler-Toledo® 821e instrument.

TGA was recorded using a TA Instruments® Q500.

The following examples are for illustrative purposes only and should not be construed as limiting the scope of the invention in any way.

EXAMPLES

Example 1

Preparation of a Crystalline Form of Ibrutinib. Designated as Form S1

Ibrutinib (0.5 g) was stirred in dimethoxyethane (5 mL) at 0° C. to 5° C. for 7 hours.

The mixture was filtered, and the solid obtained was dried under vacuum at ambient temperature for 2 hours to obtain the crystalline form of ibrutinib designated as Form S1. Yield: 0.28 g Example 2

Preparation of a Crystalline Form of Ibrutinib, Designated as Form S1

Ibrutinib (0.3 g) was stirred in dimethoxyethane (4.5 mL) at 0° C. to 5° C. for 4 hours. n-Heptane (10 mL) was added to the mixture dropwise, and stirring was continued for 3 hours at 0° C. to 5° C. The mixture was filtered, and the solid obtained was dried under vacuum at ambient temperature for 3 hours to obtain the crystalline form of ibrutinib designated as Form S1.
Yield: 0.29 g Example 3

Preparation of a Crystalline Form of Ibrutinib, Designated as Form S2

A crystalline form of ibrutinib designated as Form S1 (0.31 g, as obtained from Example 1 or Example 2) was dried at 40° C. under vacuum for 44 hours to obtain the crystalline form of ibrutinib designated as Form S2.
Yield: 0.26 g Example 4

Preparation of a Crystalline Form of Ibrutinib, Designated as Form S3

A crystalline form of ibrutinib, designated as Form S1 (0.33 g, as obtained from Example 1 or Example 2) was dried at 70° C. under vacuum for 10 hours to obtain the crystalline form of ibrutinib designated as Form S3.
Yield: 0.28 g Example 5

Preparation of an Amorphous Form of Ibrutinib, Designated as Form A1

A crystalline form of ibrutinib designated as Form S3 (0.23 g, as obtained from Example 4) was dried at 95° C. under vacuum for 2 hours to obtain the amorphous form of ibrutinib designated as Form A1.
Yield: 0.22 g Example 6

Preparation of a Crystalline Form of Ibrutinib, Designated as Form S4

A crystalline form of ibrutinib designated as Form S3 of ibrutinib (0.15 g, as obtained from Example 4) was heated at 120° C. for 2 hours to obtain the crystalline form of ibrutinib designated as Form S4.
Yield: 0.14 g Example 7

Preparation of a Crystalline Form of Ibrutinib, Designated as Form S4

An amorphous form of ibrutinib designated as Form A1 (0.15 g, as obtained from Example 5) was heated at 120° C. for 2 hours to obtain the crystalline form of ibrutinib designated as Form S4.
Yield: 0.14 g Example 8

Preparation of a Crystalline Form of Ibrutinib, Designated as Form S4

A crystalline form of ibrutinib designated as Form S1 (0.045 g, as obtained from Example 1 or Example 2) was mixed with seed crystals of a crystalline form of ibrutinib designated as Form S4 (0.005 g, as obtained from Example 6 or Example 7) and heated initially at 90° C. for 5 hours and then at 120° C. for one hour to obtain the crystalline form of ibrutinib designated as Form S4.
Yield: 0.04 g Example 9

Preparation of a Crystalline Form of Ibrutinib, Designated as Form S4

The amorphous form of ibrutinib designated as Form A1 (0.97 g, as obtained from Example 5) was mixed with seed crystals of a crystalline form of ibrutinib, designated as Form S4 (0.025 g, as obtained from Example 6 or Example 7) and heated at 120° C. for 2.5 hours to obtain the crystalline form of ibrutinib designated as Form S4.
Yield: 0.98 g Example 10

Preparation of a Crystalline Form of Ibrutinib, Designated as Form S4

Step 1:
Ibrutinib (19 g) was dissolved in dichloromethane (180 mL) by stirring at room temperature to obtain a clear solution. The solution was filtered, and the filtrate was evaporated to dryness in a rotavapor at 35° C. to 45° C. under reduced pressure. The residue was crushed to powder, and then dried further in a vacuum tray drier at 45° C. to 55° C. for 2 hours to 12 hours.
Step 2:
Seed crystals of a crystalline form of ibrutinib designated as Form S4 (400 mg, as obtained from Example 7 or Example 8) were added to n-heptane (540 mL), preheated to 67° C. to 70° C., followed by the addition of solid powder of Step 1 under stirring. The mixture was stirred at 67° C. to 70° C. for 10 minutes to 60 minutes, and then it was allowed to cool to 40° C. to 60° C. under stirring. The mixture was filtered, and the solid was dried at 45° C. to 60° C. for 6 hours to 12 hours in a vacuum tray drier to obtain the crystalline form of ibrutinib designated as Form S4.
Yield: 17 g Example 11

Preparation of a Crystalline Form of Ibrutinib, Designated as Form S4

Step 1:
Ibrutinib (19 g) was dissolved in dichloromethane (180 mL) by stirring at 45° C. to obtain a clear solution. The solution was filtered, and the filtrate was evaporated to dryness in a rotavapor at 35° C. to 45° C. under reduced pressure. The residue was crushed to powder, and then dried further in a vacuum tray drier at 45° C. to 55° C. for 2 hours to 12 hours.
Step 2:
Seed crystals of a crystalline form of ibrutinib designated as Form S4 (400 mg, as obtained from Example 7 or Example 8) were added to n-heptane (540 mL), preheated to 67° C. to 70° C., followed by the addition of the solid powder of Step 1 under stirring. The mixture was stirred at 67° C. to 70° C. for 10 minutes to 60 minutes, and then it was allowed to cool to 40° C. to 60° C. under stirring. The mixture was filtered, and the solid was dried at 45° C. to 60° C. for 6 hours to 12 hours in a vacuum tray drier to obtain the crystalline form of ibrutinib designated as Form S4.
Yield: 17 g

We claim:

1. A crystalline form of ibrutinib, designated as Form S1, characterized by an XRPD pattern having peaks at d-spacings of about 5.1, 4.5, 4.4, 4.2, and 4.0 Å and substantially as depicted in FIG. 1.

2. The crystalline form according to claim 1, further characterized by a DSC thermogram having an endothermic peak at about 102.3° C. and an exothermic peak at about 134.7° C.

3. A crystalline form of ibrutinib, designated as Form S1, characterized by an XRPD pattern having peaks at d-spacings of about 5.1, 4.5, 4.4, 4.2, and 4.0 Å and a DSC thermogram substantially as depicted in FIG. 2.

4. The crystalline form according to claim 1, further characterized by an IR absorption spectrum substantially as depicted in FIG. 3.

5. The crystalline form of ibrutinib designated as Form S1 of claim 1, made by a process comprising contacting ibrutinib with dimethoxyethane, optionally in the presence of an anti-solvent.

6. The crystalline form of ibrutinib, of Form S1 according to claim 5, wherein the anti-solvent is selected from the group consisting of heptane, hexane, cyclohexane, methylcyclohexane, and diisopropylether.

7. A crystalline form of ibrutinib, designated as Form S4, characterized by the XRPD pattern having peaks at d-spacings of 14.7, 7.5, 7.3, 6.4, 4.2, 3.8, and 3.7 A.

8. The crystalline form of claim 7, characterized by a DSC thermogram having an endothermic peak at 145° C.

9. The crystalline form of ibrutinib designated as Form S4 according to claim 7, made by a process comprising:
   a) contacting ibrutinib with a halogenated hydrocarbon; and
   b) adding seed crystals of a crystalline form of ibrutinib designated as Form S4 to obtain the crystalline form of ibrutinib designated as Form S4.

10. The crystalline form of ibrutinib designated as Form S4 according to claim 9, wherein the halogenated hydrocarbon is selected from the group consisting of dichloromethane, dichloroethane and chloroform.

11. The crystalline form according to claim 3, characterized by a DSC thermogram having an endothermic peak at about 102.3° C. and an exothermic peak at about 134.7° C.

12. The crystalline form according to claim 3, characterized by an XRPD pattern substantially as depicted in FIG. 1.

13. The crystalline form according to claim 3, characterized by an IR absorption spectrum substantially as depicted in FIG. 3.

14. The crystalline form of ibrutinib designated as Form Si of claim 3, made by a process comprising contacting ibrutinib with dimethoxyethane, optionally in the presence of an anti-solvent.

15. The crystalline form of ibrutinib of Form Si according to claim 14, wherein the anti-solvent is selected from the group consisting of heptane, hexane, cyclohexane, methylcyclohexane, and diisopropylether.

* * * * *